United States Patent [19]

Kunz et al.

[11] 4,442,117
[45] Apr. 10, 1984

[54] HOMOSERINE DERIVATIVES AND THEIR USE AS MICROBICIDES

[75] Inventors: Walter Kunz, Oberwil, Switzerland; Wolfgang Eckhardt, Lörrach, Fed. Rep. of Germany; Adolf Hubele, Magden; Peter Riebli, Basel, both of Switzerland

[73] Assignee: Ciba-Geigy Corporation, Ardsley, N.Y.

[21] Appl. No.: 199,903

[22] Filed: Oct. 23, 1980

[30] Foreign Application Priority Data

Oct. 26, 1979 [CH] Switzerland ............... 9631/79
Sep. 24, 1980 [CH] Switzerland ............... 7150/80

[51] Int. Cl.$^3$ ............... A01N 37/22; C07C 103/66; C07C 103/737
[52] U.S. Cl. .............. 424/273 R; 260/455 R; 260/507 R; 424/469; 424/273 P; 424/285; 424/300; 424/309; 424/319; 548/262; 548/336; 548/341; 548/378; 549/487; 560/10; 560/12; 560/13; 560/14; 560/16; 560/21; 560/22; 560/31; 560/32; 560/43; 560/163; 562/426; 562/427; 562/430; 562/433; 562/435; 562/437; 562/455; 562/456
[58] Field of Search ............... 260/347.2, 347.3, 347.4, 260/455 A, 507 R; 424/269, 273 R, 285, 300, 309, 319, 273 P; 548/262, 336, 341, 378; 560/10, 12, 13, 14, 16, 21, 22, 31, 32, 39, 41, 43, 163; 562/426, 427, 430, 435, 437, 448, 449, 450, 455, 456, 433; 549/487

[56] References Cited

U.S. PATENT DOCUMENTS

| | | | |
|---|---|---|---|
| 4,025,648 | 5/1977 | Hubele | 424/309 |
| 4,032,657 | 6/1977 | Moser | 424/309 |
| 4,093,738 | 6/1978 | Hubele | 424/309 |
| 4,094,990 | 6/1978 | Hubele | 424/285 |
| 4,098,895 | 7/1978 | Hubele et al. | 424/269 |
| 4,151,299 | 4/1979 | Hubele | 424/309 |
| 4,214,005 | 7/1980 | Eckhardt et al. | 424/309 |

Primary Examiner—Richard Raymond
Attorney, Agent, or Firm—Frederick H. Rabin

[57] ABSTRACT

There are described novel homoserine derivatives of the formula (I)

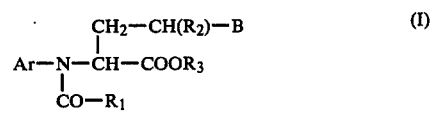

which possess valuable microbicidal properties. In the formula: Ar is substituted phenyl or naphthyl; $R_1$ is $C_2$–$C_6$ alkyl optionally interrupted by oxygen or sulfur, 2-furyl, 2-tetrahydrofuryl, 1H-1,2,4-triazolylmethyl, 1-imidazolylmethyl, 1-pyrazolylmethyl, $C_2$–$C_4$ alkenyl or cyclopropyl, each of which is optionally substituted by halogen; $R_2$ is hydrogen or methyl; $R_3$ is hydrogen or $C_1$–$C_4$ alkyl; and B is halogen or an ester, thioester, sulfonic acid ester or sulfonic acid amide group. Additionally, where B is halogen, $R_1$ may be halomethyl. The novel derivatives can be used for combating microorganisms harmful to plants, particularly for combating phytopathogenic fungi, and they have for practical requirements a very favorable curative and protective action for protecting cultivating plants, without the plants being impaired as a result of undesirable secondary effects. A notable feature is their stability to heat and to solar irradiation. They can be used in practice on their own or in the form of pesticidal compositions.

49 Claims, No Drawings

HOMOSERINE DERIVATIVES AND THEIR USE AS MICROBICIDES

The present invention relates to homoserine derivatives of the formula I, to their production, and to their use as microbicides,

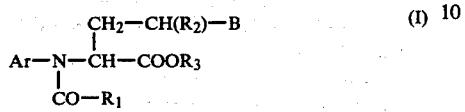

wherein $R_1$ is an aliphatic chain of 2 to 6 carbon atoms which is optionally interrupted by an oxygen or sulfur atom, or it is a 2-furyl, 2-tetrahydrofuryl, 1H-1,2,4-triazolylmethyl, 1-imidazolylmethyl, 1-pyrazolylmethyl, $C_2$–$C_4$-alkenyl or cyclopropyl group, each of which is unsubstituted or is substituted by halogen, or wherein, when B is halogen, $R_1$ is a halomethyl group, $R_2$ is hydrogen or methyl, $R_3$ is hydrogen or $C_1$–$C_4$-alkyl, and Ar is

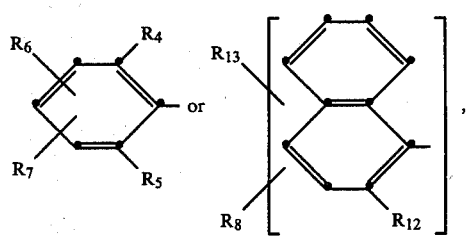

in which $R_4$ is $C_1$–$C_3$-alkyl, $C_1$–$C_3$-alkoxy or halogen, $R_5$ is $C_1$–$C_3$-alkyl, $C_1$–$C_3$-alkoxy, $NH_2$, halogen or $NO_2$, $R_6$ is hydrogen, $NO_2$, $NH_2$, $C_1$–$C_3$-alkyl, $C_1$–$C_3$-alkoxy or halogen, $R_7$ and $R_8$ are hydrogen or methyl, $R_{12}$ is methyl, $NO_2$ or $NH_2$, $R_{13}$ is hydrogen, methyl, $NO_2$ or $NH_2$, and B is one of the following groups

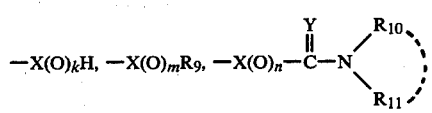

or halogen, wherein X and Y independently of one another are each oxygen or sulfur, and, when X is sulfur, k has the value nought or 3, and n and m are nought, 1 or 2, whilst when X is oxygen k, m and n are always nought, $R_9$ is a $C_1$–$C_5$-alkyl group which is unsubstituted or substituted by halogen, $C_1$–$C_3$-alkoxy or $C_1$–$C_3$-alkylthio, $R_{10}$ is hydrogen, methyl or ethyl, $R_{11}$ is a $C_1$–$C_5$-alkyl group which is unsubstituted or substituted by halogen, or $R_{11}$ is a phenyl group which is unsubstituted or substituted by halogen, methyl, trifluoromethyl or nitro, or $R_{10}$ and $R_{11}$ together with the nitrogen atom to which they are bound form an imidazole or 1,2,4-triazole ring.

The present invention relates also to compounds of the formula I, to their production, and to their use as microbicides, wherein Ar is

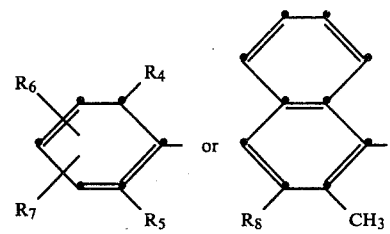

$R_1$, $R_2$, $R_3$, $R_4$ and B have the meanings defined hereinbefore, and $R_5$ is $C_1$–$C_3$-alkyl, $C_1$–$C_3$-alkoxy or halogen, $R_6$ is hydrogen, $C_1$–$C_3$-alkyl, $C_1$–$C_3$-alkoxy or halogen, and $R_7$ and $R_8$ are hydrogen or methyl.

By alkyl or alkyl part of another substituent are meant, depending on the given number of C atoms, for example the following groups: methyl, ethyl, propyl, butyl, pentyl or hexyl, as well as isomers thereof, such as isopropyl, isobutyl, tert-butyl, isopentyl, and so forth.

Alkenyl is for example vinyl, 1-propenyl, allyl, 1-butenyl, 2-butenyl, and the like.

These are given purely as examples and in no way do they constitute any limitation.

Halogen is fluorine, chlorine, bromine or iodine, preferably chlorine, bromine or iodine.

Compounds of the formula I are very valuable active substances against harmful microorganisms.

Preferred microbicidal active substances of the formula I are those of which the substituents represent the following groups:

for $R_1$:
(a) halomethyl, $C_1$–$C_3$-alkoxymethyl, $C_2$–$C_3$-alkenyl, cyclopropyl, 2-furyl, 2-tetrahydrofuryl, 1-H-1,2,4-trizolylmethyl or 1-imidazolylmethyl,
(b) halomethyl, $C_1$–$C_2$-alkoxymethyl, $C_2$–$C_3$-alkenyl, 2-furyl or 2-tetrahydrofuryl;

for $R_2$: hydrogen or methyl;
for $R_3$: hydrogen or $C_1$–$C_3$-alkyl;
for $R_4$: methyl, ethyl or Cl;
for $R_5$: methyl, ethyl, methoxy or Cl;
for $R_6$:
(a) hydrogen, methyl, ethyl, methoxy, Cl, Br, $NH_2$ or $NO_2$,
(b) hydrogen, 3-methyl, 3-ethyl, 3-Cl, 4-Cl, 3-methoxy, 3-$NO_2$ or 3-$NH_2$;

for $R_7$: hydrogen or methyl;
for $R_8$:
(a) hydrogen or methyl,
(b) hydrogen or 3-methyl;
for $R_{12}$: $CH_3$ or $NO_2$;
for $R_{13}$: hydrogen or $NO_2$;
for B: hydroxyl, chlorine, bromine or iodine, or when B is: $X(O)_kH$, —$X(O)_mR_9$ or

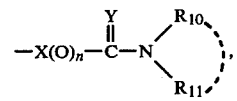

for X and Y: oxygen, and k=m=n=nought,
for $R_9$: $C_1$–$C_3$-alkyl,
for $R_{10}$: hydrogen, methyl or ethyl,
for $R_{11}$:
(a) $C_1$–$C_3$-alkyl or phenyl each unsubstituted or substituted by halogen,
(b) $C_1$–$C_3$-alkyl or phenyl, for

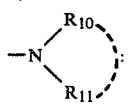

1,2,4-triazolyl or imidazolyl.

The following groups of compounds of the formula I are preferred:

A preferred group is formed by substituted phenyl compounds of the formula I (Ar=substituted phenyl), wherein $R_1$ is $C_1$–$C_3$-alkoxymethyl, 2-furyl or 2-tetrahydrofuryl, $R_2$ and $R_3$ are hydrogen, B is OH, SH or $SO_3H$, $R_4$ is $C_1$–$C_3$-alkyl, $C_1$–$C_3$-alkoxy or halogen, $R_5$ is $C_1$–$C_3$-alkyl, $C_1$–$C_3$-alkoxy, halogen or nitro, $R_6$ is hydrogen or $C_1$–$C_3$-alkyl, and $R_7$ is hydrogen or methyl. This preferred group is to be designated as subgroup Ia.

A further preferred group of substituted phenyl compounds of the formula I is that wherein $R_1$ is $C_1$–$C_3$-alkoxymethyl, 2-furyl or 2-tetrahydrofuryl, $R_2$ is hydrogen, $R_3$ is $C_1$–$C_3$-alkyl, B is $OR_9$, $R_9$ is a $C_1$–$C_3$-alkyl group which is unsubstituted or substituted by halogen, $R_4$ is $C_1$–$C_3$-alkyl, $C_1$–$C_3$-alkoxy or halogen, $R_5$ is $C_1$–$C_3$-alkyl, $C_1$–$C_3$-alkoxy or halogen, $R_6$ is hydrogen or $C_1$–$C_3$-alkyl, and $R_7$ is hydrogen or methyl. This preferred group is to be designated as subgroup Ib.

A group of particularly preferred compounds of the formula I comprises those wherein Ar is a substituted phenyl group, $R_1$ is $C_1$–$C_2$-alkoxymethyl or 2-tetrahydrofuryl, $R_2$ is hydrogen, $R_3$ is hydrogen or methyl, B is either OH or methoxy, $R_4$ is methyl, $R_5$ is methyl, chlorine, $NO_2$ or $NH_2$, $R_6$ is hydrogen, methyl, chlorine, $NO_2$ or $NH_2$, and $R_7$ is hydrogen or methyl. This particularly preferred group is to be designated as subgroup Ic.

A further group of especially preferred compounds of the formula I is formed by those compounds wherein Ar is a substituted α-naphthyl group, $R_1$ is $C_1$–$C_2$-alkoxymethyl or 2-tetrahydrofuryl, $R_2$ is hydrogen, $R_3$ is hydrogen or methyl, B is either OH or methoxy, $R_8$ is hydrogen or 3-methyl, $R_{12}$ is methyl, $NO_2$ or $NH_2$, and $R_{13}$ is hydrogen, methyl, $NO_2$ or $NH_2$. This particularly preferred group is to be designated as subgroup Id.

Within the subgroup Id, $R_{13}$ is preferably hydrogen, 4—$NO_2$ or 4—$NH_2$.

A separate group of fungicides comprises those compounds of the subgroup Ic and those of the subgroup Id wherein $R_1$ is tetrahydrofuryl.

The following individual compounds are particularly preferred:
N-(2,6-dimethylphenyl)-N-methoxyacetyl-homoserine-methyl ester,
N-(2,6-dimethylphenyl)-N-methoxyacetyl-homoserine-ethyl ester,
N-(2,6-dimethylphenyl)-N-methoxyacetyl-4-(N'-ethylcarbamoyloxy)-2-aminobutyric acid methyl ester,
N-(2,6-dimethylphenyl)-N-methoxyacetyl-[(4-imidazol-1-yl)-carbonyloxy]-butyric acid methyl ester,
N-(2-chloro-6-methoxyphenyl)-N-methoxyacetyl-homoserine-methyl ester,
N-(2,3,6-trimethylphenyl)-N-methoxyacetyl-4-(N'-methylcarbamoyloxy)-2-aminobutyric acid methyl ester,
N-(2,3,6-trimethylphenyl)-N-methoxyacetyl-homoserine-methyl ester,
N-(2,3,6-trimethylphenyl)-N-methoxyacetyl-homoserine-ethyl ester,
N-(2,6-dimethyl-3-chlorophenyl)-N-methoxyacetyl-homoserine-methyl ester,
N-(2,3,6-trimethylphenyl)-N-methoxyacetyl-4-methoxy-2-aminobutyric acid methyl ester,
N-(2-methylnaphthyl)-N-methoxyacetyl-homoserine,
N-(2-methylnaphthyl)-N-methoxyacetyl-4-methoxy-2-aminobutyric acid methyl ester,
N-(2-methylnaphthyl)-N-methoxyacetyl-homoserine-methyl ester,
N-(2-methylnaphthyl)-N-(2-tetrahydrofurylcarbonyl)-homoserine,
N-(2-methylnaphthyl)-N-(2-tetrahydrofurylcarbonyl)-homoserine-methyl ester,
N-(2-methylnaphthyl)-N-methoxyacetyl)-4-(N'-methylcarbamoyloxy)-2-aminobutyric acid methyl ester,
N-(2,3-dimethylnaphthyl)-N-methoxyacetyl-homoserine-methyl ester, and
N-(2-methyl-6-nitrophenyl)-N-methoxyacetyl-homoserine-methyl ester.

The compounds of the formula I can be produced by a whole series of reaction variants, such as by those shown in the following reaction diagram and subsequently given in detail. In the formulae II to VII, the symbols $R_1$ to $R_{13}$, X, Y, k, n, m and B have the meanings defined under the formula I, Hal, Hal' and Hal" independently of one another are each halogen, preferably chlorine, bromine or iodine, M denotes a metal ion, preferably an alkali metal ion or alkaline-earth metal ion, and Q signifies one of the customary groups that can be split off, for example halogen, especially chlorine or bromine, benzenesulfonyl, p-tosyl, trifluoroacetyl, or lower alkylsulfonyl, such as mesyl.

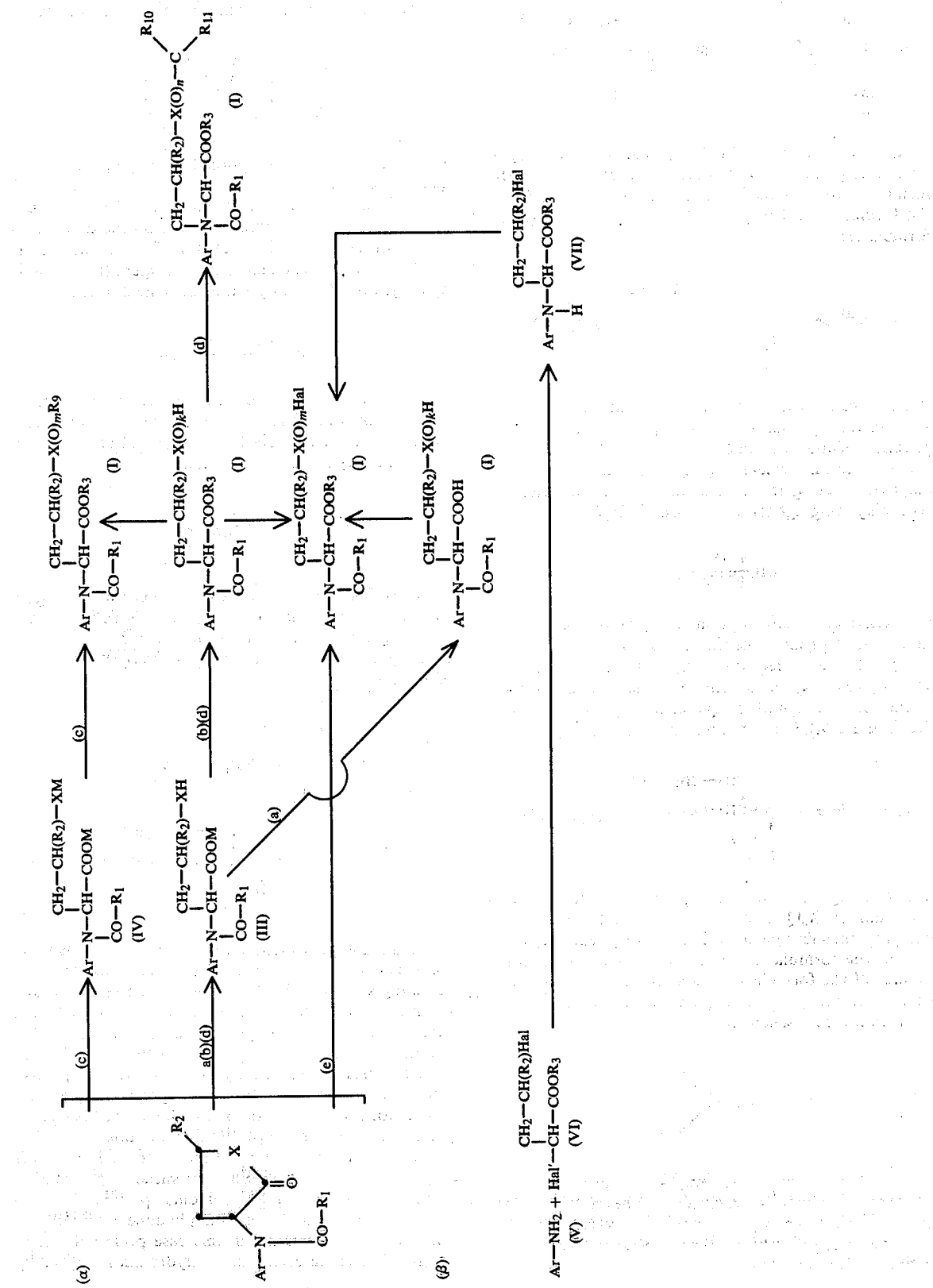

The compounds of the formula I are produced according to the invention (α) by ring opening of the heterocyclic substituent from compounds of the formula II

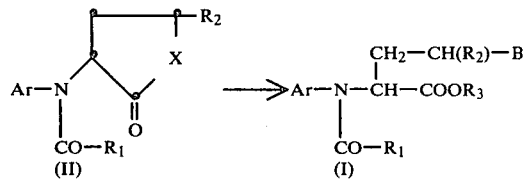

(a) in the case where B is $X(O)_kH$ and $R_3$ is hydrogen by reacting lactone or thiolactone derivatives of the formula II with the equimolar amount of a compound of the formula MOH to give carboxylic acid salts of the formula III

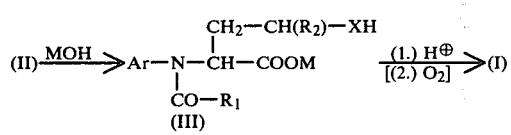

and converting these by gentle protonation, and where X is sulfur optionally by subsequent oxidation, into products of the formula I; or (b) in the case where B is $X(O)_kH$ and $R_3$ is $C_1$–$C_4$-alkyl by reacting the intermediates of the formula III with alkylating agents of the formula $R_3Q$

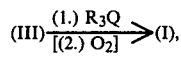

and where X is sulfur optionally by subsequent oxidation, to give products of the formula I; or (c) in the case where B is $—X(O)_mR_9$ and $R_3$ is $C_1$–$C_4$-alkyl by reacting the lactone or thiolactone derivatives of the formula II with 2 equivalents of a compound of the formula MOH to obtain salts of the formula IV

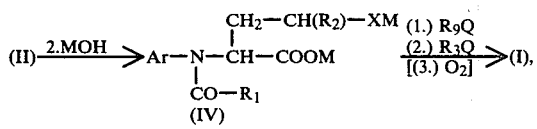

and reacting these with compounds of the formulae $R_9Q$ and/or $R_3Q$, and where X is sulfur optionally carrying out subsequent oxidation, or by reacting products of the formula I, wherein B is —XH, with compounds of the formula $R_9Q$, and where X is sulfur optionally carrying out subsequent oxidation; or (d) in the case where B is

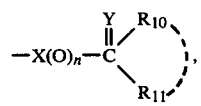

and $R_3$ is $C_1$–$C_4$-alkyl by reacting the products of the formula I obtained by variant (b), wherein B is —XH, either with isocyanates or isothiocyanates of the formula $R_{11}NCY$, or with isocyanic or isothiocyanic acid halides of the formula

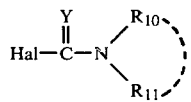

or with urea or thiourea compounds of the formula

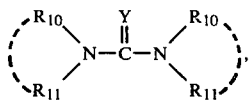

and where X is sulfur optionally carrying out subsequent oxidation; or (e) in the case where B is halogen and $R_3$ is $C_1$–$C_4$-alkyl by reacting the lactone or thiolactone derivatives of the formula II, in the presence of an alcohol of the formula $R_3OH$, with a halogenating agent (for example hydrogen halide, thionyl chloride, and so forth)

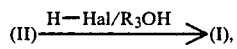

and optionally performing a halogen exchange by reaction with an alkali halide, or by converting in products of the formula I wherein B is —XH the last-mentioned group, in a hydrohalic acid solution, into halogen

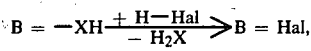

or (β) by N-alkylation, in the case where B is halogen, by converting an aniline of the general formula V with a dihalogen compound VI into an intermediate VII, and reacting this by acylation to give compounds of the formula I

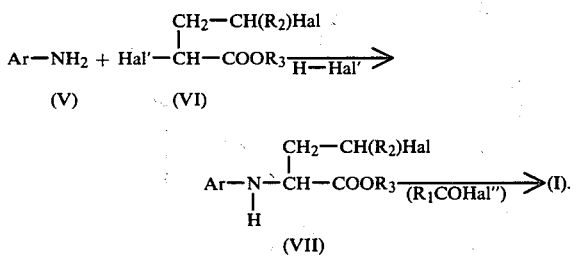

It is advantageous with all production variants to use solvents which are inert to all the reactants, and it is also advantageous, in order to accelerate the reaction rate, to raise the reaction temperature and/or to use suitable catalysts. It is of advantage in some cases to add a condensation agent or binding agent to the reaction mixture. In certain cases it may be preferable to perform some reaction steps in a protective-gas atmosphere.

The following conditions can be of advantage in performing the various production variants:

The alkaline ring opening of the starting compound II is performed in the production variant (a) advantageously in strongly polar solvents, preferably in alcohol/water mixtures, for example aqueous methanol. The hydroxides used are in this case preferably alkali metal or alkaline-earth metal hydroxides, especially sodium hydroxide. The reaction temperature in this reaction can be within the range of $-10°$ to $+100°$ C. The subsequent protonation [III→I] is advantageously carried out under gentle conditions, preferably with the aid of acid ion-exchanger resins.

The esterification of the COOH group in compounds of the formula III, defined as production variant (b), is performed with compounds of the formula $R_3Q$, wherein $R_3$ is as defined under the formula I and Q is one of the customary removable groups of an alkylating agent, for example halogen, especially chlorine or bromine, benzenesulfonyl, p-tosyl, trifluoroacetyl or lower alkyl, such as mesyl. There are advantageously used dipolar aprotic solvents, for example dimethylformamide, dimethylsulfoxide or hexamethylphosphoric acid triamide; but also other hydrocarbons, particularly halogenated hydrocarbons, which are inert to the compound III, are suitable as reaction media. This reaction can be performed in a temperature range of $0°$ to $+100°$ C., preferably $+10°$ to $+40°$ C.

The solvents and reagents used for the production variant (c) are advantageously aqueous solutions of the alcohols $R_9OH$ and/or $R_3OH$, wherein $R_9$ and $R_3$ can be identical and have the same meanings as given under the formula I. Suitable hydroxides are in this case mainly alkali metal or alkaline-earth metal hydroxides, especially NaOH. The reaction temperature in this reaction can be within the range of $-10°$ to $+100°$ C.

Variant (d), which is suitable in particular for producing compounds of the formula I wherein B is

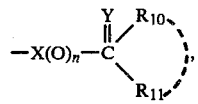

is preferably performed in inert aprotic solvents. Suitable solvents are halogenated hydrocarbons, such as dichloromethane, chloroform, carbon tetrachloride, 1,2-dichloroethane, tetrachloroethylene, chlorobenzene, and so forth, and also aromatic hydrocarbons, such as benzene, toluene, xylenes or nitriles, such as acetonitrile or propionitrile, and esters, such as ethyl acetate, butyl acetate, and so forth. Also mixtures of solvents of this kind can be used. The temperature for this reaction can be within the range of $0°$ to $80°$ C., preferably $0°$ to $30°$ C. It is advantageous in some cases to add a catalyst: suitable catalysts are for example tertiary amines, such as trialkylamines (trimethylamine, triethylamine or tripropylamine), and also diazabicyclo(2,2,2)octane. Certain advantages are to be gained particularly in the case of this variant by performing the reaction in a protective-gas atmosphere, for example under nitrogen.

In the case of variant (e), the reaction of the starting compound II is preferably performed in alcohols of the formula $R_3OH$ wherein $R_3$ is $C_1-C_4$-alkyl. An addition of a further inert solvent is possible. The reaction temperature depends with this production variant on the type of halogenating agent employed. If for example a hydrogen halide is used, the temperature can be within a range of $-20°$ to $120°$ C., preferably however between $0°$ and $80°$ C. If however the halogenating agent used is a thionyl halide, the temperature in general is within the range of $-20°$ to $+30°$ C. Halogen in this variant is fluorine, chlorine, bromine and iodine, preferably chlorine and iodine. Iodides are in general obtainable by halogen exchange reactions, for example with potassium iodide, from the corresponding chlorides.

The N-alkylation ($\beta$) is performed advantageously in one of the customary inert organic solvents, for example in benzene, toluene, xylenes, carbon tetrachloride, tetrachloroethylene, diethyl ether, t-butylmethyl ether, tetrahydrofuran, and so forth. It can prove to be of advantage to perform the reaction in the presence of a proton acceptor, such as $NaHCO_3$ or $Na_2CO_3$. Suitable acylating agents are for example compounds of the formula $R_1COHal''$ or $(R_1CO)_2O$, wherein $R_1$ has the meanings defined under the formula I.

All compounds of the formula I in which X is a nonoxidised sulfur atom can be subsequently oxidised with oxidising agents, for example peroxy acids, such as $H_2O_2$, perbenzoic acid, metachloroperbenzoic acid or $HJO_4$, or also with potassium permanganate. An HS group can be converted into an $HO_3S$ group, a thioether into a sulfoxide or further into a sulfone.

The production process in all its variants $\alpha$[a, b, c, d and e] and $\beta$ forms an essential part of the invention.

The compounds of the formula I have, in the position adjacent to the nitrogen atom, one asymmetric centre (*) and in the case where $R_2$ is $CH_3$ a second asymmetric centre (**) adjacent to $R_2$

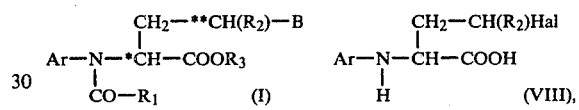

and can be split in the customary manner into optical isomers or diastereoisomers; thus for example by fractional crystallisation or chromatographic separation of a salt of VIII with an optically active base (for example D-α-phenylethylamine) and subsequent acylation of the optically active compounds VIII to I. The optical isomers or diastereoisomers I have varying microbicical activities.

There can be present depending on substitution also further asymmetrical carbon atoms in the molecule.

Independently of the stated optical isomerism, there is observed an atropisomerism around the $>$N—Ar axis when Ar is substituted unsymmetrically with respect to this axis.

When no specific synthesis is carried out to isolate pure isomers, a product of the formula I is usually obtained as a mixture of all these possible isomers.

The starting compounds of the formulae V, VI and VII are generally known and are produced by commonly known processes.

Compounds which are embraced by the general formula II are for the most part known from the German Offenlegungsschrift No. 2,804,299 (=GB No. 1,577,702). Individual compounds of the formula II which are not known can be obtained by one of the production processes mentioned therein.

Some lactone derivatives of the formula II are also mentioned in the German Offenlegungsschrift No. 2,724,786. Lactone and thiolactone derivatives of the formula II are mentioned as fungicides in the German Offenlegungsschrift No. 2,845,454.

The intermediates of the formulae III and IV are novel: they too have a fungicidal action and likewise form part of the subject matter of the present invention.

Compared with the described starting materials of the formula II, the homoserine derivatives of the formula I according to the invention have a clearly improved activity spectrum, particularly with regard to the combating of phytopathogenic fungi and to the capacity for resisting heat and solar irradiation.

The Examples which follow are intended to further illustrate the invention without in any way limiting the scope thereof. Percentages and parts are always by weight, and temperature values are in degrees Centigrade. Except where otherwise specifically stated, the racemic mixture is meant in all cases where an active substance of the formula I is mentioned.

PRODUCTION EXAMPLES

Example 1

Production of

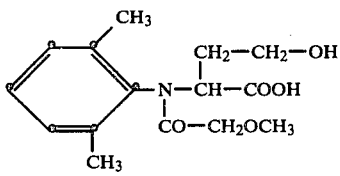
(1.1)

N-(2,6-Dimethylphenyl)-N-methoxyacetyl-homoserine 11.0 g (0.04 mol) of 3-[N-(methoxyacetyl)-N-(2,6-dimethylphenyl)]-amino-tetrahydro-2-furanone are dissolved in 50 ml of methanol, and a solution of 1.6 g of sodium hydroxide in 20 ml of water is added. Stirring is maintained for 12 hours at room temperature; the solution is then concentrated by evaporation, and the salt obtained is protonated with an acid ion-exchanger column. The aqueous eluate is extracted with methylene chloride; the combined extracts are subsequently washed with water, dried over sodium sulfate and concentrated by evaporation. The residue is recrystallised from ethyl acetate/ligroin to thus obtain colourless crystals, m.p. 150°–152°.

Further compounds of the formula I can be produced in an analogous manner, particularly those of the following subgroup Ia:

TABLE 1

($R_2=H$; $R_3=H$;)

| Comp. No. | Ar | B | $R_1$ | Physical constants |
|---|---|---|---|---|
| 1.1 | $C_6H_3(CH_3)_2(2,6)$ | OH | $CH_2OCH_3$ | m.p. 150–152° C. |
| 1.2 | $C_6H_2(CH_3)_3(2,3,6)$ | OH | $CH_2OCH_3$ | m.p. 155–157° C. |
| 1.3 | $C_6H_3(CH_3)_2(2,6)$ | SH | $CH_2OCH_3$ | |
| 1.4 | $C_6H_2(CH_3)_2(2,6)Cl(3)$ | OH | $CH_2OCH_3$ | |
| 1.5 | $C_6H_3(CH_3)_2(2,6)$ | OH | 2-tetrahydro-furyl | m.p. 166–170° C. |
| 1.6 | α-naphthyl-$CH_3(2)$ | OH | $CH_2OC_2H_5$ | |
| 1.7 | $C_6H_3(CH_3)_2(2,6)$ | OH | cyclopropyl | |
| 1.8 | $C_6H_3(CH_3)_2(2,6)$ | OH | $CH=CH-CH_3$ | |
| 1.9 | $C_6H_3(CH_3)_2(2,6)$ | OH | $CH_2OC_2H_5$ | |
| 1.10 | $C_6H_3CH_3(2)C_2H_5(6)$ | OH | $CH_2OCH_3$ | |
| 1.11 | α-naphthyl-$CH_3(2)$ | SH | $CH_2OCH_3$ | |
| 1.12 | α-naphthyl-$CH_3(2)$ | OH | $CH_2OC_2H_5$ | |
| 1.13 | $C_6H(CH_3)_4(2,3,5,6)$ | OH | 2-Furyl | |
| 1.14 | $C_6H_2(CH_3)_3(2,3,6)$ | OH | 2-Furyl | |
| 1.15 | $C_6H_3(CH_3)(2)NO_2(6)$ | OH | $CH_2OCH_3$ | m.p. 110–114° C. |
| 1.16 | $C_6H_2(CH_3)_3(2,3,6)$ | SH | cyclopropyl | |
| 1.17 | α-naphthyl$(CH_3)_2(2,3)$ | OH | $CH_2OC_2H_5$ | |
| 1.18 | $C_6H_3(CH_3)_2(2,6)$ | OH | $CH_2OCH_3$ | |
| 1.19 | $C_6H_3(CH_3)_2(2,6)$ | SH | $CH_2OCH_3$ | |
| 1.20 | $C_6H_2(CH_3)_3(2,3,6)$ | OH | $CH_2OC_2H_5$ | |
| 1.21 | $C_6H_3(CH_3)_2(2,6)$ | $SO_3H$ | $CH_2OCH_3$ | |
| 1.22 | α-naphthyl-$CH_3(2)$ | $SO_3H$ | $CH_2OCH_3$ | |
| 1.23 | $C_6H_2(CH_3)_3(2,3,6)$ | $SO_3H$ | cyclopropyl | |
| 1.24 | α-naphthyl-$(CH_3)_2(2,3)$ | OH | $CH_2OCH_3$ | m.p. 160–161° |
| 1.25 | α-naphthyl-$CH_3(2)$ | OH | $CH_2OCH_3$ | m.p. 125–134° |
| 1.26 | α-naphthyl-$CH_3(2)$ | OH | 2-tetrahydro-furyl | |
| 1.27 | α-naphthyl-$CH_3(2)$-$NO_2(4)$ | OH | 2-tetrahydro-furyl | |
| 1.28 | α-naphthyl-$CH_3(2)$-$NH_2(4)$ | OH | 2-tetrahydro-furyl | |
| 1.29 | α-naphthyl-$(CH_3)_2$ (2,3)-$NO_2(4)$ | OH | 2-tetrahydro-furyl | |
| 1.30 | α-naphthyl-$(CH_3)_2$ (2,3)-$NH_2(4)$ | OH | 2-tetrahydro-furyl | |
| 1.31 | α-naphthyl-$(CH_3)_2$ (2,3)-$NO_2(4)$ | OH | $CH_2OCH_3$ | |
| 1.32 | α-naphthyl-$(CH_3)_2$ (2,3)-$NH_2(4)$ | OH | $CH_2OCH_3$ | |
| 1.33 | α-naphthyl-$(CH_3)(2)$-$NO_2(4)$ | OH | $CH_2OCH_3$ | |
| 1.34 | α-naphthyl-$(CH_3)(2)$-$NO_2(6)$ | OH | $CH_2OCH_3$ | |

EXAMPLE 2a

Production of

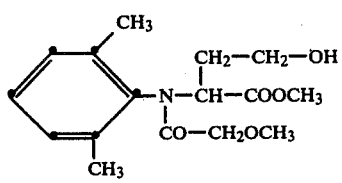 (2.1)

N-(2,6-Dimethylphenyl)-N-methoxyacetyl-homoserine methyl ester 11.0 g (0.04 mol) of 3-[N-(methoxyacetyl)-N-(2,6-dimethylphenyl)]-aminotetrahydro-2-furanone are dissolved in 50 ml of methanol, and a solution of 1.6 g of sodium hydroxide in 20 ml of water is added, and stirring is maintained for 12 hours. The solution is then concentrated by evaporation, and the residue is dissolved in 75 ml of abs. dimethylformamide. 3.2 ml of methyl iodide are added dropwise, stirring is continued for 24 hours at room temperature, and a further 1.8 ml of methyl iodide are added dropwise. After 24 hours' stirring at room temperature, the solvent is removed in vacuo, and the residue is taken up in methylene chloride; the solution is washed with water, dried over sodium sulfate and concentrated by evaporation. The dry residue is taken up in ether, precipitated with petroleum ether, filtered off, and digested twice with ether/petroleum ether. The crystals obtained melt at 81°–83°.

EXAMPLE 2b

Production of

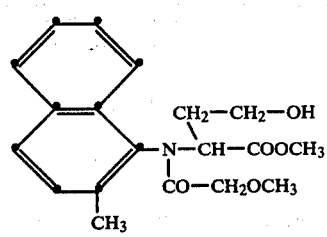 (Comp. No. 2.19)

N-(2-Methylnaphthyl)-N-methoxyacetyl-homoserine methyl ester (α) 15.7 g of N-(2-methylnaphthyl)-N-methoxyacetal-N-(2-oxo-tetrahydrofuran-3-yl)-amine are dissolved in 100 ml of methanol. 10 ml of sodium hydroxide solution (30%) are added dropwise at 0° during 10 minutes, and stirring is maintained for 3 hours at room temperature. The solution is afterwards concentrated in a rotary evaporator, and the disodium salt of N-(2-methylnaphthyl)-N-methoxyacetylhomoserine remaining is dried at 90° under high vacuum.

(β) 0.083 mol of the disodium salt obtained is dissolved in 100 ml of dimethylformamide, and 14.1 g of methyl iodide are added at 0°–5° during 15 minutes. Stirring is maintained for 6 hours at room temperature, the solution is then concentrated in a rotary evaporator, the residue is stirred up with 50 ml of methylene chloride, and the organic phase is poured into ice water; it is separated, extracted twice with 25 ml of methylene chloride each time, and the combined extracts are dried over sodium sulfate. After concentrating the solution by evaporation, the residue is dissolved in 30 ml of hot chloroform and, after cooling, a small amount of diethyl ether is added; the yield is 14 g of crystalline final product, m.p. 132°–137°.

Further compounds of the formula I can be produced in an analogous manner:

TABLE 2

($R_2$=H)

| Comp. No. | Ar | B | $R_1$ | $R_3$ | Physical constants |
|---|---|---|---|---|---|
| 2.1 | $C_6H_3(CH_3)_2(2,6)$ | OH | $CH_2OCH_3$ | $CH_3$ | m.p. 81–83° |
| 2.2 | $C_6H_3(CH_3)_2(2,6)$ | OH | $CH_2OCH_3$ | $C_2H_5$ | m.p. 87–90° |
| 2.3 | $C_6H_2(CH_3)_3(2,3,6)$ | OH | $CH_2OCH_3$ | $CH_3$ | resin |
| 2.4 | $C_6H_2(CH_3)_2(2,6)Cl(3)$ | OH | $CH_2OCH_3$ | $CH_3$ | resin |
| 2.5 | $C_6H_2(CH_3)_3(2,3,6)$ | OH | $CH_2OCH_3$ | $C_2H_5$ | m.p. 98–102° |
| 2.6 | $C_6H_3(CH_3)_2(2,6)$ | SH | $CH_2OCH_3$ | $CH_3$ | m.p. 118–121° |
| 2.7 | $C_6H(CH_3)_4(2,3,5,6)$ | OH | $CH_2OCH_3$ | $CH_3$ | |
| 2.8 | $C_6H_3(CH_3)_2(2,6)$ | OH | $CH_2OCH_3$ | $C_4H_9-n$ | |
| 2.9 | $C_6H_3(CH_3)_2(2,6)$ | OH | $CH_2OCH_3$ | $C_3H_7-i$ | |
| 2.10 | $C_6H_3OCH_3(2)Cl(6)$ | OH | $CH_2OCH_3$ | $CH_3$ | resin |
| 2.11 | $C_6H_3OCH_3(2)CH_3(6)$ | OH | $CH_2OCH_3$ | $CH_3$ | |
| 2.12 | $C_6H_3(CH_3)_2(2,6)$ | OH | 2-furyl | $CH_3$ | |
| 2.13 | $C_6H_3(CH_3)_2(2,6)$ | OH | 2-tetra-hydrofuryl | $CH_3$ | m.p. 104–110° |
| 2.14 | $C_6H_3(CH_3)_2(2,6)$ | OH | cyclopropyl | $CH_3$ | resin |
| 2.15 | $C_6H_2(CH_3)_3(2,3,6)$ | OH | $CH_2OC_2H_5$ | $CH_3$ | |
| 2.16 | $C_6H_2(CH_3)_2(2,6)Br(4)$ | SH | $CH=CH-CH_3$ | $C_2H_5$ | |
| 2.17 | $C_6H_3(CH_3)_2(2,6)$ | OH | 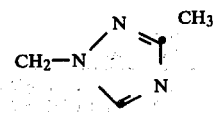 | $CH_3$ | |
| 2.18 | $C_6H_2(CH_3)_3(2,3,6)$ | OH | 2-tetra-hydrofuryl | | |

TABLE 2-continued (R₂=H)

| Comp. No. | Ar | B | R₁ | R₃ | Physical constants |
|---|---|---|---|---|---|
| 2.19 | α-naphthyl(CH₃)(2) | OH | CH₂OCH₃ | CH₃ | m.p. 132–137° |
| 2.20 | α-naphthyl(CH₃)₂ (2,3) | SH | CH₂OCH₃ | CH₃ | |
| 2.21 | C₆H₃(CH₃)₂(2,6) | OH | CH₂OCH₃ | —CH₂—CH(CH₃)—CH₃ | |
| 2.22 | α-naphthyl-CH₃(2)OCH₃(3) | OH | CH₂OCH₃ | CH₃ | |
| 2.23 | α-naphthyl-CH₃(2)Cl(3) | OH | CH₂OCH₃ | CH₃ | |
| 2.24 | α-naphthyl-CH₃(2) | OH | CH—N(triazine ring) | CH₃ | |
| 2.25 | C₆H₂(CH₃)₂(2,6)OCH₃(3) | OH | CH₂OC₂H₅ | CH₃ | |
| 2.26 | C₆H₃(CH₃)₂(2,6) | OH | CH₂OCH₃ | CH₃ | |
| 2.27 | C₆H₂(CH₃)₃(2,3,6) | OH | 2-tetrahydrofuryl | CH₃ | resin |
| 2.28 | C₆H₃(CH₃)₂(2,6) | SO₃H | CH₂OCH₃ | CH₃ | |
| 2.29 | C₆H₂(CH₃)₃(2,3,6) | SO₃H | CH₂OCH₃ | CH₃ | |
| 2.30 | α-naphthyl(CH₃)(2,3) | SO₃H | CH₂OCH₃ | CH₃ | |
| 2.31 | C₆H₃CH₃(2)C₂H₅(6) | OH | 2-tetrahydrofuryl | CH₃ | resin |
| 2.32 | C₆H₃CH₃(2)NO₂(6) | OH | CH₂OCH₃ | CH₃ | resin |
| 2.33 | α-naphthyl(CH₃)₂(2,3) | OH | CH₂OCH₃ | CH₃ | m.p. 137° |
| 2.34 | α-naphthyl(CH₃)₂(2,3) | OH | CH₂OCH₃ | C₂H₅ | m.p. 115° |
| 2.35 | α-naphthyl(CH₃)₂(2,3)NO₂(4) | OH | CH₂OCH₃ | CH₃ | |
| 2.36 | α-naphthyl(CH₃)₂(2,3)NH₂(4) | OH | CH₂OCH₃ | CH₃ | |
| 2.37 | α-naphthyl(CH₃)₂(2,3)NO₂(4) | OH | CH₂OCH₃ | C₂H₅ | |
| 2.38 | α-naphthyl(CH₃)₂(2,3)NO₂(4) | OH | 2-tetrahydrofuryl | CH₃ | |
| 2.39 | α-naphthyl(CH₃)₂(2,3)NO₂(4) | 2-tetrahydrofuryl | C₂H₅ | | |
| 2.40 | α-naphthyl(CH₃)₂(2,3)NH₂(4) | OH | 2-tetrahydrofuryl | CH₃ | |
| 2.41 | α-naphthyl(CH₃)₂(2,3)NO₂(6) | OH | CH₂OCH₃ | CH₃ | |
| 2.42 | α-naphthyl-CH₃(2) | OH | 2-tetrahydrofuryl | CH₃ | m.p. 141–144° |
| 2.43 | α-naphthyl-CH₃(2) | OH | 2-tetrahydrofuryl | C₂H₅ | |
| 2.44 | α-naphthyl-CH₃(2)NO₂(4) | OH | 2-tetrahydrofuryl | CH₃ | |
| 2.45 | α-naphthyl-CH₃(2)NO₂(4) | OH | CH₂OCH₃ | CH₃ | |
| 2.46 | α-naphthyl-CH₃(2)NH₂(4) | OH | CH₂OCH₃ | CH₃ | |
| 2.47 | α-naphthyl-CH₃(2)NO₂(4) | OH | CH₃OCH₃ | C₂H₅ | |
| 2.48 | α-naphthyl-CH₃(2)NH₂(4) | OH | 2-tetrahydrofuryl | CH₃ | |

EXAMPLE 3

Production of

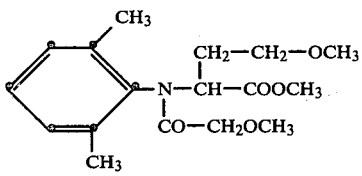

(3.1)

N-(2,6-Dimethylphenyl)-N-methoxyacetyl-4-methoxy-2-aminobutyric acid methyl ester 4.0 g of sodium hydroxide in 20 ml of water are added to 13.8 g of 3-[(N-methoxyacetyl)-N-(2,6-dimethylphenyl)]-amino-tetrahydro-2-furanone in 100 ml of methanol; the mixture is left to stand for 1 hour at room temperature and is then concentrated by evaporation. The residue is dried in vacuo, subsequently taken up in 100 ml of dimethylformamide and, with stirring, 14 ml of methyl iodide are added dropwise, in the course of which the temperature rises to about 35° and a precipitate is formed. Stirring is continued for 12 hours at room temperature, the solvent is evaporated off and water is added to the residue. After several extractions with methylene chloride, the combined extracts are repeatedly washed with water, dried over sodium sulfate and concentrated by evaporation. Distillation at 164°–168°/0.8 Torr yields a viscous oil.

Further compounds of the formula I can be produced in an analogous manner, especially those of the following subgroups Ic and Id:

TABLE 3

($R_2$=H; B=X(O)$_m$R₉)

| Comp. No. | Ar | —X(O)$_m$— | R₁ | R₃ | R₉ | Physical constants |
|---|---|---|---|---|---|---|
| 3.1 | C₆H₃(CH₃)₂(2,6) | O | CH₂OCH₃ | CH₃ | CH₃ | b.p. 164–168°/0,8 Torr |
| 3.2 | C₆H₃(CH₃)₂(2,6) | O | CH₂OCH₃ | C₂H₅ | C₂H₅ | b.p. 195°/0.8 Torr |
| 3.3 | C₆H₃(CH₃)₂(2,6) | S | CH₂OCH₃ | CH₃ | CH₃ | m.p. 51–52° |
| 3.4 | C₆H₂(CH₃)₃(2,3,6) | O | CH₂OCH₃ | CH₃ | CH₃ | resin |
| 3.5 | C₆H₃(CH₃)₂(2,6) | O | 2-tetrahydrofuryl | CH₃ | CH₃ | |

TABLE 3-continued ($R_2$=H; B=X(O)$_m$$R_9$)

| Comp. No. | Ar | —X(O)$_m$— | $R_1$ | $R_3$ | $R_9$ | Physical constants |
|---|---|---|---|---|---|---|
| 3.6 | $C_6H_2(CH_3)_2(2,6)Cl(3)$ | O | $CH_2OCH_3$ | $CH_3$ | $CH_3$ | |
| 3.7 | $C_6H_3CH_3(2)C_2H_5(6)$ | O | $CH_2OCH_3$ | $C_2H_5$ | $C_2H_5$ | |
| 3.8 | $C_6H(CH_3)_4(2,3,5,6)$ | O | 2-furyl | $CH_3$ | $CH_3$ | |
| 3.9 | α-naphthyl-$CH_3$(2) | O | 2-tetrahydrofuryl | $CH_3$ | $CH_3$ | |
| 3.10 | α-naphthyl-$CH_3$(2) | O | $CH_2OCH_3$ | $CH_3$ | $CH_3$ | resin |
| 3.11 | $C_6H_3Cl(2)OCH_3(6)$ | O | $CH_2OCH_3$ | $C_3H_7$—n | $C_3H_7$—n | |
| 3.12 | $C_6H_3Cl(2)OCH_3(6)$ | O | 2-tetrahydrofuryl | $CH_3$ | $CH_3$ | |
| 3.12 | α-naphthyl-$CH_3$(2) | S | 2-furyl | $CH_3$ | $CH_3$ | |
| 3.14 | $C_6H_3(CH_3)_2(2,6)$ | O | cyclopropyl | $C_2H_5$ | $CH_3$ | |
| 3.15 | $C_6H_3(CH_3)_2(2,6)$ | O | $CH_2OCH_3$ | $CH_3$ | $C_2H_5$ | |
| 3.16 | $C_6H_3(CH_3)_2(2,6)$ | O | 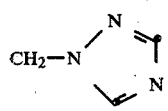 | $CH_3$ | $CH_3$ | |
| 3.17 | $C_6H_3(CH_3)_2(2,6)$ | O | $CH_2OCH_3$ | $CH_3$ | $CH_3$ | |
| 3.18 | $C_6H_3(CH_3)_2(2,6)$ | O | $CH_2OCH_3$ | $C_2H_5$ | $C_2H_5$ | |
| 3.19 | $C_6H_3(CH_3)_2(2,6)$ | O | 2-tetrahydrofuryl | $CH_3$ | $CH_3$ | |
| 3.20 | $C_6H_3(CH_3)_2(2,6)$ | —S(O)— | $CH_2OCH_3$ | $CH_3$ | $CH_3$ | |
| 3.21 | $C_6H_3(CH_3)_2(2,6)$ | —S(O)$_2$— | $CH_2OCH_3$ | $CH_3$ | $CH_3$ | |
| 3.22 | $C_6H_2(CH_3)_3(2,3,6)$ | —S(O)— | $CH_2OCH_3$ | $CH_3$ | $CH_3$ | |
| 3.23 | $C_6H_2(CH_3)_3(2,3,6)$ | —S(O)$_2$— | $CH_2OCH_3$ | $CH_3$ | $CH_3$ | |
| 3.24 | α-naphthyl-$CH_3$(2)-$NO_2$(4) | O | $CH_2OCH_3$ | $CH_3$ | $CH_3$ | |
| 3.25 | α-naphthyl-$CH_3$(2)-$NO_2$(4) | O | 2-tetrahydrofuryl | $CH_3$ | $CH_3$ | |
| 3.26 | α-naphthyl-$CH_3$(2)-$NH_2$(4) | O | 2-tetrahydrofuryl | $CH_3$ | $CH_3$ | |
| 3.27 | α-naphthyl-$CH_3$(2)-$NH_2$(4) | O | $CH_2OCH_3$ | $CH_3$ | $CH_3$ | |
| 3.28 | α-naphthyl($CH_3$)$_2$—(2,3)$NO_2$(4) | O | $CH_2OCH_3$ | $CH_3$ | $CH_3$ | |
| 3.29 | α-naphthyl($CH_3$)$_2$(2,3)-$NO_2$(4) | O | 2-tetrahydrofuryl | $CH_3$ | $CH_3$ | |
| 3.30 | α-naphthyl($CH_3$)$_2$(2,3)-$NH_2$(4) | O | 2-tetrahydrofuryl | $CH_3$ | $CH_3$ | |
| 3.31 | α-naphthyl($CH_3$)$_2$(2,3)-$NH_2$(4) | O | $CH_2OCH_3$ | $CH_3$ | $CH_3$ | |

EXAMPLE 4

(a) Production of

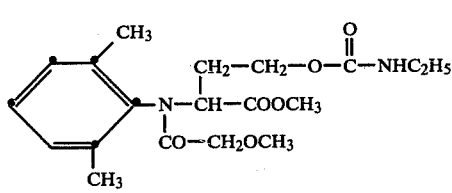
(4.3)

N-(2,6-Dimethylphenyl)-N-methoxyacetyl-4-(N-ethyl-carbamoyloxy)-2-aminobutyric acid methyl ester 9.3 g of N-(2,6-dimethylphenyl)-N-methoxyacetyl-homoserinemethyl ester are dissolved in 200 ml of absolute tetrahydrofuran, and a catalytical amount of 1,4-diazabicyclo(2,2,2)octane is added. 2.6 g of ethylisocyanate are added dropwise with stirring and ice-cooling, and stirring is continued for 20 hours at 40°-50°; the solution is concentrated by evaporation, and the resin remaining is digested with petroleum ether, whereupon it solidifies. The crystals obtained are filtered off, their melting point being 56°-60°.

(b) Production of

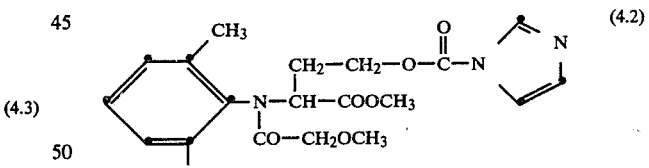
(4.2)

N-(2,6-Dimethylphenyl)-N-methoxyacetyl-[4-imidazol-1-yl)-carbonyloxy]-butyric acid methyl ester 9.3 g of N-(2,6-dimethylphenyl)-N-methoxyacetyl-homoserinemethyl ester are dissolved in 200 ml of abs. dioxane, and 7.3 g of N,N-carbonyldiimidazole are added in a nitrogen atmosphere. The resulting solution is stirred overnight at room temperature; it is then poured into ice-water and extracted with methylene chloride. The extracts are washed with water, dried over sodium sulfate, and the solvent is removed in vacuo. After being dissolved in ether and treated with active charcoal, the pure product obtained is in the form of a viscous resin.

Further compounds of the formula I can be produced in an analogous manner and are listed in Table 4:

TABLE 4

$$(B = -X(O)_n-\overset{\overset{Y}{\|}}{C}-N\begin{smallmatrix}R_{10}\\ \\R_{11}\end{smallmatrix}; R_2 = H)$$

| Comp. No. | Ar | $R_1$ | $R_3$ | B | Physical constants |
|---|---|---|---|---|---|
| 4.1 | $C_6H_3(CH_3)_2(2,6)$ | $CH_2OCH_3$ | $CH_3$ | $-OCO-NHC_4H_9-n$ | oil |
| 4.2 | $C_6H_3(CH_3)_2(2,6)$ | $CH_2OCH_3$ | $CH_3$ | $-OCO-N\!\!<\!\!\text{imidazolyl}$ | resin |
| 4.3 | $C_6H_3(CH_3)_2(2,6)$ | $CH_2OCH_3$ | $CH_3$ | $-OCO-NHC_2H_5$ | m.p. 56–60° |
| 4.4 | $C_6H_3(CH_3)_2(2,6)$ | $CH_2OCH_3$ | $CH_3$ | $-OCO-NHCH_3$ | m.p. 99–104° |
| 4.5 | $C_6H_2(CH_3)_3(2,3,6)$ | $CH_2OCH_3$ | $CH_3$ | $-OCO-NH-CH(CH_3)_2$ | resin |
| 4.6 | $C_6H_3(CH_3)_2(2,6)$ | $CH_2OCH_3$ | $CH_3$ | $-OCO-NH-C_6H_3Cl_2(3,5)$ | m.p. 129–130° |
| 4.7 | $C_6H_2(CH_3)_2(2,6)Cl(3)$ | $CH_2OCH_3$ | $CH_3$ | $-OCO-NHC_2H_5$ | resin |
| 4.8 | $C_6H(CH_3)_4(2,3,5,6)$ | $CH_2OCH_3$ | $CH_3$ | $-OCO-N\!\!<\!\!\text{imidazolyl}$ | |
| 4.9 | $C_6H_2(CH_3)_3(2,3,6)$ | $CH_2OCH_3$ | $CH_3$ | $-OCO-NHCH_3$ | resin |
| 4.10 | $C_6H_3CH_3(2)Cl(6)$ | $CH_2OCH_3$ | $CH_3$ | $-OCO-NHC_3H_7-n$ | |
| 4.11 | $C_6H_3CH_3(2)OCH_3(6)$ | $CH_2OCH_3$ | $CH_3$ | $-OCO-N\!\!<\!\!\text{triazolyl}$ | |
| 4.12 | $C_6H_3OCH_3(2)Cl(6)$ | $CH_2OCH_3$ | $CH_3$ | $-OCO-N\!\!<\!\!\text{imidazolyl}$ | |
| 4.13 | $C_6H_3(CH_3)_2(2,6)$ | $CH_2OCH_3$ | $C_2H_5$ | $-OCO-NHC_2H_5$ | |
| 4.14 | α-naphthyl-$CH_3(2)$ | $CH_2OCH_3$ | $CH_3$ | $-OCO-NH-CH_3$ | resin |
| 4.15 | α-naphthyl$(CH_3)_2(2,3)$ | $CH_2OCH_3$ | $C_2H_5$ | $-OCO-NHCH_3$ | |
| 4.16 | α-naphthyl-$CH_3(2)Cl(3)$ | $CH_2OCH_3$ | $CH_3$ | $-OCO-NHCH_3$ | |
| 4.17 | $C_6H_3(CH_3)_2(2,6)$ | $CH_2OCH_3$ | $CH_3$ | $-OCO-NHC_5H_{11}-n$ | |
| 4.18 | $C_6H_3(C_2H_5)_2(2,6)$ | $CH_2OCH_3$ | $CH_3$ | $-OCO-NHC_2H_5$ | |
| 4.19 | $C_6H_3CH_3(2)C_2H_5(6)$ | $CH_2OCH_3$ | $CH_3$ | $-OCO-NHCH_3$ | |
| 4.20 | $C_6H_3(CH_3)_2(2,6)$ | 2-tetrahydrofuryl | $CH_3$ | $-OCO-NHCH_3$ | |
| 4.21 | $C_6H_3(CH_3)_2(2,6)$ | 2-tetrahydrofuryl | $CH_3$ | $-OCO-NHC_2H_5$ | |
| 4.22 | $C_6H_3(CH_3)_2(2,6)$ | 2-tetrahydrofuryl | $CH_3$ | $-OCO-NHC_3H_7-i$ | |
| 4.23 | $C_6H_3(CH_3)_2(2,6)$ | 2-tetrahydrofuryl | $C_2H_5$ | $-OCO-NHC_2H_5$ | |
| 4.24 | $C_6H_3(CH_3)_2(2,6)$ | 2-tetrahydrofuryl | $C_3H_7-n$ | $-OCO-N\!\!<\!\!\text{imidazolyl}$ | |
| 4.25 | $C_6H_3(CH_3)_2(2,6)$ | 2-tetrahydrofuryl | $CH_3$ | $-OCO-N\!\!<\!\!\text{imidazolyl}$ | |
| 4.26 | $C_6H_3(CH_3)_2(2,6)$ | 2-tetrahydrofuryl | $C_4H_9-n$ | $-OCO-N\!\!<\!\!\text{imidazolyl}$ | |
| 4.27 | $C_6H_3(CH_3)_2(2,6)$ | 2-tetrahydrofuryl | $CH_3$ | $-OCO-NHC_6H_4Cl(4)$ | |
| 4.28 | $C_6H_3(CH_3)_2(2,6)$ | 2-tetrahydrofuryl | $CH_3$ | $-OCO-NHC_6H_5$ | |
| 4.29 | $C_6H_3(CH_3)_2(2,6)$ | $CH_2OCH_3$ | $CH_3$ | $-OCO-NHC_6H_5$ | |
| 4.30 | $C_6H_3(CH_3)_2(2,6)$ | $CH_2OCH_3$ | $CH_3$ | $-OCO-NHC_6H_4CH_3(4)$ | |
| 4.31 | $C_6H_3(CH_3)_2(2,6)$ | $CH_2OCH_3$ | $CH_3$ | $-OCO-N(CH_3)_2$ | |
| 4.32 | $C_6H_2(CH_3)_3(2,3,6)$ | $CH_2OCH_3$ | $CH_3$ | $-OCO-NHC_6H_5$ | m.p. 138° |
| 4.33 | $C_6H_2(CH_3)_3(2,3,6)$ | $CH_2OCH_3$ | $CH_3$ | $-OCO-NHC_6H_4F(4)$ | m.p. 134° |

TABLE 4-continued

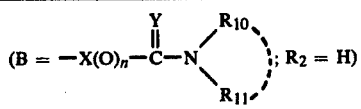

$(B = -X(O)_n-\overset{Y}{\underset{\|}{C}}-N\overset{R_{10}}{\underset{R_{11}}{\diagdown}}; R_2 = H)$

| Comp. No. | Ar | $R_1$ | $R_3$ | B | Physical constants |
|---|---|---|---|---|---|
| 4.34 | α-naphthyl(CH₃)₂(2,3)NO₂(4) | CH₂OCH₃ | CH₃ | —OCONHCH₃ | |
| 4.35 | α-naphthyl-(CH₃)₂(2,3)NO₂(4) | 2-tetrahydrofuryl | CH₃ | —OCO—NHCH₃ | |
| 4.36 | C₆H₃(CH₃)₂(2,6) | 2-furyl | CH₃ | —OCO—NHC₃ | |
| 4.37 | C₆H₃(CH₃)₂(2,6) | cyclopropyl | CH₃ | —OCO—NHC₂H₅ | |
| 4.38 | C₆H₃(CH₃)₂(2,6) | —CH═CHCH₃ | CH₃ | —OCO—NH(CH₃)₂ | |
| 4.39 | C₆H₂(CH₃)₂(2,6)Br(4) | (furyl-Br) | C₂H₅ | —OCO—NHCH₃ | |
| 4.40 | α-naphthyl-CH₃(2) | 2-Furyl | CH₃ | —OCO—NHC₃H₇—n | |
| 4.41 | C₆H₃(CH₃)₂(2,6) | CH₂OCH₃ | CH₃ | —OCO—NH(CH₂)₂Cl | resin |
| 4.42 | C₆H₃(CH₃)₂(2,6) | CH₂OC₂H₅ | CH₃ | —OCO—NHC₂H₅ | |
| 4.43 | C₆H₃(CH₃)₂(2,6) | CH₂OC₂H₅ | CH₃ | —OCO—N(CH₃)₂ | |
| 4.44 | C₆H₃(CH₃)₂(2,6) | CH₂OC₂H₅ | CH₃ | —OCO—N(imidazolyl) | |
| 4.45 | C₆H₃Cl(2)OCH₃(6) | CH₂OCH₃ | CH₃ | —OCO—NHCH₃ | resin |
| 4.46 | C₆H₂(CH₃)₃(2,3,6) | CH₂—N(1,2,4-triazolyl) | CH₃ | —OCO—NHC₂H₅ | |
| 4.47 | C₆H₃(CH₃)₂(2,6) | CH₂—N(1,2,4-triazolyl) | CH₃ | —OCO—NHCH₃ | |
| 4.48 | C₆H₃(CH₃)₂(2,6) | CH₂—N(1,2,4-triazolyl) | CH₃ | —OCO—N(imidazolyl) | |
| 4.49 | α-naphthyl-CH₃(2) | CH₂—N(1,2,4-triazolyl) | CH₃ | —OCO—NHC₂H₅ | |
| 4.50 | α-naphthyl-CH₃(2) | CH₂OCH₃ | CH₃ | —SCO—NHC₂H₅ | |
| 4.51 | C₆H₃(CH₃)₂(2,6) | CH₂OCH₃ | CH₃ | —SCS—NHCH₃ | resin |
| 4.52 | C₆H₃(CH₃)₂(2,6) | CH₂OCH₃ | CH₃ | —SCS—N(CH₃)₂ | resin |
| 4.53 | C₆H₃(CH₃)₂(2,6) | CH₂OCH₃ | CH₃ | —SCS—N(C₂H₅)₂ | resin |
| 4.54 | C₆H₃(CH₃)₂(2,6) | 2-tetrahydrofuryl | CH₃ | —SCS—NHC₂H₅ | viscous |
| 4.55 | C₆H₃(CH₃)₂(2,6) | CH₂—N(1,2,4-triazolyl) | CH₃ | —SCS—NHCH₃ | viscous |
| 4.56 | C₆H₃(CH₃)₂(2,6) | CH₂OCH₃ | CH₃ | —OCO—NHC₂H₅ | resin |
| 4.57 | α-naphthyl-CH₃(2) | 2-tetrahydrofuryl | CH₃ | —OCO—NHCH₃ | viscous |
| 4.58 | α-naphthyl-CH₃(2)NO₂(4) | 2-tetrahydrofuryl | CH₃ | —OCO—NHCH₃ | resin |
| 4.59 | α-naphthyl-CH₃(2)NO₂(4) | CH₂OCH₃ | CH₃ | —OCO—NHCH₃ | resin |

EXAMPLE 5

(a) Production of

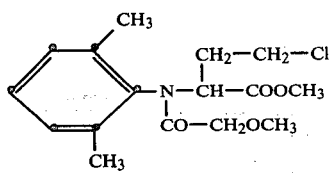 (5.1)

N-(2,6-Dimethylphenyl)-N-methoxyacetyl-2-amino-4-chlorobutyric acid methyl ester 27.7 g of 3-[(N-methoxyacetyl)-N-(2,6-dimethylphenyl)]-amino-tetrahydro-2-furanone are dissolved in 150 ml of methanol at 40° to 50°; the solution is subsequently cooled and saturated at 0° to 5° with gaseous hydrogen chloride. After the solution has stood for 3 days at room temperature, it is heated to 55° and left for 24 hours at this temperature. The solution is then concentrated by evaporation, the residue is dissolved in methylene chloride and washed with ice-water; and the solution is dried over sodium sulfate and concentrated by evaporation. Unreacted starting material is insoluble in diethyl ether: it is precipitated therein and filtered off. Removal of the ether leaves crystals of the compound No. 5.1, which melt at 70°-72° after recrystallisation from petrolether.

(b) Production of

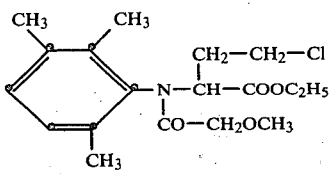 (5.3)

N-(2,3,6-Trimethylphenyl)-N-methoxyacetyl-2-amino-4-chlorobutyric acid ethyl ester 20.4 g of 3-[(N-methoxyacetyl)-N-(2,3,6-trimethylphenyl)]-aminotetrahydro-2-furanone are dissolved in 150 ml of ethanol, and 12.5 g of thionyl chloride are added dropwise with stirring. The solution is then heated and refluxed for 4 hours; a further 10 g of thionyl chloride are added, and refluxing is continued for 2 hours. The solution is concentrated by evaporation to leave a resin, which is purified through a silica gel column (chloroform/ether 1:1). Compound No. 5.3 precipitates as a viscous resin.

Further compounds of the formula I can be produced analogously to the production variants 5a and 5b:

TABLE 5

(B = Hal; $R_2$ = H)

| Comp. No. | Ar | B | $R_1$ | $R_3$ | Physical constants |
|---|---|---|---|---|---|
| 5.1 | $C_6H_3(CH_3)_2(2,6)$ | Cl | $CH_2OCH_3$ | $CH_3$ | m.p. 70-72 |
| 5.2 | $C_6H_3(CH_3)_2(2,6)$ | Cl | $CH_2OCH_3$ | $C_2H_5$ | viscous oil |
| 5.3 | $C_6H_2(CH_3)_3(2,3,6)$ | Cl | $CH_2OCH_3$ | $C_2H_5$ | resin |
| 5.4 | $C_6H_2(CH_3)_2(2,6)(Cl)(3)$ | Cl | $CH_2OCH_3$ | $C_2H_5$ | resin |
| 5.5 | $C_6H_3(CH_3)_2(2,6)$ | Br | $CH_2OCH_3$ | $CH_3$ | |
| 5.6 | $C_6H_3(CH_3)_2(2,6)$ | Br | $CH_2OCH_3$ | $C_2H_5$ | $n_D^{16}$ 1.5326 |
| 5.7 | $C_6H_3(CH_3)_2(2,6)$ | I | $CH_2OCH_3$ | $CH_3$ | |
| 5.8 | $C_6H_3(CH_3)_2(2,6)$ | I | $CH_2OCH_3$ | $C_2H_5$ | |
| 5.9 | $C_6H_3(CH_3)_2(2,6)$ | Cl | $CH_2OCH_3$ | $C_3H_7$—n | |
| 5.10 | $C_6H_3(CH_3)_2(2,6)$ | Cl | $CH_2OCH_3$ | $C_4H_9$—n | |
| 5.11 | $C_6H_3(CH_3)_2(2,6)$ | Cl | $CH_2OC_2H_5$ | $CH_3$ | |
| 5.12 | $C_6H_3(CH_3)_2(2,6)$ | Cl | $CH_2OC_2H_5$ | $C_2H_5$ | |
| 5.13 | $C_6H_3(CH_3)_2(2,6)$ | Cl | 2-tetrahydrofuryl | $CH_3$ | |
| 5.14 | $C_6H_3(CH_3)_2(2,6)$ | I | 2-tetrahydrofuryl | $CH_3$ | |
| 5.15 | $C_6H_3(CH_3)_2(2,6)$ | Cl | 2-tetrahydrofuryl | $C_2H_5$ | |
| 5.16 | $C_6H_3(CH_3)_2(2,6)$ | Cl | 2-furyl | $CH_3$ | |
| 5.17 | $C_6H_3(CH_3)_2(2,6)$ | Cl | 2-furyl | $C_2H_5$ | |
| 5.18 | $C_6H_3(CH_3)_2(2,6)$ | Cl | $CH_2SCH_3$ | $CH_3$ | |
| 5.15 | $C_6H_3(CH_3)_2(2,6)$ | Cl | cyclopropyl | $C_2H_5$ | |
| 5.20 | $C_6H_3(CH_3)_2(2,6)$ | I | cyclopropyl | $CH_3$ | |
| 5.21 | $C_6H_3(CH_3)_2(2,6)$ | Cl | —CH=CH—$CH_3$ | $CH_3$ | |
| 5.22 | $C_6H_2(CH_3)_3(2,3,6)$ | Br | 2-tetrahydrofuryl | $CH_3$ | |
| 5.23 | $C_6H_2(CH_3)_2(2,6)Cl(3)$ | Br | 2-tetrahydrofuryl | $CH_3$ | |
| 5.24 | $C_6H_2(CH_3)_2(2,6)Cl(3)$ | Cl | 2-tetrahydrofuryl | $C_2H_5$ | |
| 5.25 | $C_6H_2(CH_3)_2(2,6)Cl(3)$ | Cl | 2-tetrahydrofuryl | $C_4H_9$—n | |
| 5.26 | $C_6H_2(CH_3)_3(2,3,6)$ | Cl | $CH_2OC_2H_5$ | $CH_3$ | |
| 5.27 | $C_6H(CH_3)_4(2,3,5,6)$ | Cl | $CH_2OCH_3$ | $C_2H_5$ | |
| 5.28 | $C_6H_3OCH_3(2)Cl(6)$ | Cl | $CH_2OCH_3$ | $C_2H_5$ | resin |
| 5.29 | $C_6H_3OCH_3(2)CH_3(6)$ | Cl | $CH_2OCH_3$ | $CH_3$ | |
| 5.30 | $C_6H_3OCH_3(2)CH_3(6)$ | I | $CH_2OCH_3$ | $CH_3$ | |
| 5.31 | $C_6H_2(CH_3)_2(2,6)Br(4)$ | Cl | 2-furyl | $CH_3$ | |
| 5.32 | α-naphthyl-$CH_3(2)$ | Cl | 2-tetrahydrofuryl | $C_2H_5$ | |
| 5.33 | α-naphthyl-$CH_3(2)$ | Cl | $CH_2OCH_3$ | $C_2H_5$ | resin |
| 5.34 | α-naphthyl$(CH_3)_2(2,3)$ | I | $CH_2OC_2H_5$ | $CH_3$ | |
| 5.35 | $C_6H_3(CH_3)_2(2,6)$ | Cl | $CH_2Cl$ | $CH_3$ | |
| 5.36 | $C_6H_3(CH_3)_2(2,6)$ | I | $CH_2J$ | $CH_3$ | |
| 5.37 | $C_6H_3(CH_3)_2(2,6)$ | Br | $CH_3Br$ | $C_2H_5$ | |
| 5.38 | $C_6H(CH_3)_4(2,3,5,6)$ | Cl | $CH_2Cl$ | $C_2H_5$ | |
| 5.39 | α-napthyl-$CH_3(2)$ | Cl | $CH_3Cl$ | $C_2H_5$ | |
| 5.40 | α-napthyl-$CH_3(2)$ | Cl | $CH_2Cl$ | $CH_3$ | |

It has now been found that compounds of the formula I surprisingly exhibit a very favourable microbicidal spectrum for practical requirements. They can be used for example to protect cultivated crops.

The main field of application for compounds of the formula I is the combating of harmful microorganisms, particularly phytopathogenic fungi. Thus the compounds of the formula I have a very favourable curative and preventive action for protecting cultivated plants without the plants being impaired as a result of undesirable side effects. Cultivated plants within the scope of the present invention are for example: cereals (wheat, barley, rye, oats and rice); beet (sugar beet and fodder beet); pomaceous, stone and soft fruit (apples, pears, plums, peaches, almonds, cherries, strawberries, raspberries and blackberries); leguminous plants (beans, lentils, peas and soya bean); oil crops (rape, mustard, poppy, olives, sunflower, coconut, castor-oil plants, cocoa and peanuts); cucurbitaceae (cucumbers, pumpkins and melons); fibre plants (cotton, flax, hemp and jute); citrus fruits (oranges, lemons, grapefruit and mandarines); vegetable varieties, (spinach, lettuce, asparagus, cabbage varieties, carrots, onions, tomatoes, potatoes and paprika); or plants such as maize, tobacco, nuts, coffee, sugar cane, tea, grapevines, hops, banana and natural rubber plants, and ornamental plants.

Microorganisms occurring on plants or on parts of plants (fruit, blossom, foliage, stalks, tubers or roots) of the said crops and of related cultivated crops can be inhibited or destroyed with the active substances of the formula I, and also parts of plants subsequently growing remain preserved from such microorganisms. Active substances of the formula I are effective against a whole series of phytopathogenic fungi, including for example the Erysiphe and Venturia pathogens belonging to the Ascomycetes family; and they are effective also against the Oomycetes belonging to the Phycomycetes class, such as Phytophtora, (Pseudo) Peronospora, Plasmopara and Pythium. Some representatives of the classes of substances also have insecticidal and bactericidal activity.

The active substances of the present invention can also be used as dressing agents for the treatment of seed (fruit, tubers and grain), and of plant cuttings to protect them against fungus infections, and also against harmful microorganisms occurring in the soil.

The invention thus relates also to the use of the compounds of formula I for combating phytopathogenic micoorganisms or for preventing infection on plants.

For combating the said microorganisms, the compounds of the formula I can be used on their own or together with suitable carriers and/or other additives. Suitable carriers and additives can be solid or liquid and they correspond to the substances customarily employed in formulation practice, for example natural or regenerated mineral substances, solvents, dispersing agents, wetting agents, adhesives, thickeners, binders or fertilisers. Active substances of the formula I can be used also in admixture with for example pesticidal preparations or with preparations improving plant growth.

The nature of preparations of this type is further illustrated by the following examples.

The content of active substance in commercial compositions is between 0.0001 and 90%.

For application, the compounds of the formula I can be in the following forms:

Solid preparations

Dusts and scattering agents contain in general up to 10% of active substance. A dust can consist for example of 5 parts of active substance and 95 parts of an additive, such as talcum; or of 2 parts of active substance, 1 part of highly dispersed silicic acid and 97 parts of talcum. Further mixtures with these and other carriers and additives common in formulation practice are also conceivable. These dusts and scattering agents are produced by mixing and grinding the active substances with the carriers and additives, and in this form they can be applied by dusting.

Granulates, such as coated, impregnated and homogeneous granulates and also pellets, usually contain 1 to 80% of active substance. A 5% granulate can thus be composed of for example 5 parts of active substance, 0.25 part of epoxidised vegetable oil, 0.25 part of cetyl polyglycol ether, 3.50 parts of polyethylene glycol and 91 parts of kaolin (preferred particle size 0.3–0.8 mm). The manner of producing the granulate can be as follows: The active substance is mixed with the vegetable oil, the mixture is dissolved in 6 parts of acetone, and the polyethylene glycol and cetyl polyglycol ether are added. The solution obtained is sprayed onto kaolin, and the acetone is subsequently evaporated off in vacuo. A microgranulate of this type is advantageously used for combating soil fungi.

Liquid preparations

A distinction is generally made between active-substance concentrates, which are dispersible or soluble in water, and aerosols. Active-substance concentrates dispersible in water include for example wettable powders and pastes, which usually contain 25–90% of active substance in commercial packings, and 0.01 to 15% of active substance in ready-for-use solutions. Emulsion concentrates contain 10 to 50% of active substance, and solution concentrates contain in ready-for-use solution 0.001 to 20% of active substance. A 70% wettable powder can thus be composed of for example 70 parts of active substance, 5 parts of sodium dibutyl-naphthalene sulfonate, 3 parts of naphthalenesulfonic acid/phenolsulfonic acid/formaldehyde condensate (in the mixture ratio of 3:2:1), 10 parts of kaolin and 12 parts of chalk, for example Champagne chalk. A 40% wettable powder can consist for example of the following substances: 40 parts of active substance, 5 parts of sodium lignin sulfonate, 1 part of sodium dibutyl-naphthalene sulfonate and 54 parts of silicic acid. A 25% wettable powder can be produced in different ways. It can be composed for example of: 25 parts of active substance, 4.5 parts of calcium lignin sulfonate, 1.9 parts of chalk, for example Champagne chalk/hydroxyethylene cellulose mixture (1:1), 1.5 parts of sodium dibutyl-naphthalene sulfonate, 19.5 parts of silicic acid, 19.5 parts of Champagne chalk and 28.1 parts of kaolin. A 25% wettable powder can also consist of for example: 25 parts of active substance, 2.5 parts of isooctylphenoxy-polyoxyethylene-ethanol, 1.7 parts of Champagne chalk/hydroxyethyl cellulose mixture (1:1), 8.3 parts of sodium silicate, 16.5 parts of kieselguhr and 46 parts of kaolin. A 10% wettable powder can be produced for example from: 10 parts of active substance, 3 parts of a mixture of the sodium salts of saturated fatty alcohol sulfonates, 5 parts of naphthalenesulfonic acid/formaldehyde condensate and 82 parts of kaolin. Other wettable powders can be in the form of mixtures of 5 to 30% of active substance together with 5 parts of an absorbent carrier material, such as silicic acid, 55 to 80 parts of a carrier, such as kaolin, and a dispersing-agent mixture consisting of 5 parts of sodium-aryl sulfonate and 5 parts of an alkylaryl polyglycol ether. A 25% emulsion concentrate can contain for example the following emulsifiable substances: 25 parts of active substance, 2.5 parts of epoxidised vegetable oil, 10 parts of an alkylarylsulfonate/fatty alcohol polyglycol ether mixture, 5 parts of dimethylformamide and 57.5 parts of xylene. Emulsions of the required application concentration can be prepared from such concentrates by dilution with water, and these emulsions are particularly suitable for leaf application. It is moreover possible to produce further wettable powders having other mixture ratios and containing other carriers and additives customarily used in formulation practice. The active substances are intimately mixed in suitable mixers with the stated additives, and subsequently ground on the appropriate mills and rollers. Wettable powders having excellent wetting and suspension properties are obtained; the wettable powders can be diluted with water to obtain suspensions of the required concentration, and these are particularly suitable for leaf application.

Compositions which contain, as described above, as active ingredient a compound of the formula I, for example compound No. 1.6, 1.17, 1.24 to 1.34, 2.1 to 2.6, 2.10, 2.19, 2.32 to 2.48, 3.1, 3.4, 3.9, 3.10, 3.25 to 3.31, 4.2 to 4.4, 4.9 or 4.14, can be used very successfully against harmful microorganisms.

BIOLOGICAL EXAMPLES

Example 6: Action against *Erysiphe graminis* on barley plants

Residual protective action

Barley plants about 8 cm in height were sprayed with a spray liquor prepared as described above from wettable powder of the active substance (0.02% of active substance), for example one of the compounds from Tables 1 to 5. After 3-4 hours, the treated plants were dusted with conidiospores of the fungus. The infested barley plants were kept in a greenhouse at about 22°, and the fungus infection was assessed after 10 days. Compared with the infection on untreated control plants, the infection on the plants treated with the spray liquors containing as active ingredient an active substance of the formula I, for example compound No. 3.1, 3.2, 4.4, 5.1 or 5.3, had been prevented almost completely.

EXAMPLE 7

Action against *Venturia inaequalis* on apple plants

Residual protective action

Apple seedlings having about 5 developed leaves were sprayed with a spray liquor prepared according to one of the above Examples from wettable powder of the active substance (0.06% of active substance, for example one of the compounds from Tables 1 to 5). After 24 hours, the treated plants were infested with a conidiospore suspension of the fungus. The plants were then incubated for 5 days with 90-100% relative humidity, and were kept for a further 10 days in a greenhouse at 20°-24°. The extent of scab infection was assessed 15 days after infestation. Spray liquors containing as active substance one of the compounds from Tables 1 to 5 (for example compound No. 2.2, 4.3 or 4.9), prevented fungus infection virtually completely.

EXAMPLE 8

Action against *Phytophthora infestans* on tomato plants (a) Residual protective action After 3-weeks' cultivation, tomato plants were sprayed with a spray liquor prepared, as described in the foregoing, from wettable powder of the active substance (0.02% of active substance, for example one of the compounds from Tables 1 to 5). After 24 hours, the treated plants were infested with a suspension of sporangia of the fungus. An assessment of fungus infection was made after incubation of the infested plants for 5 days at 20° with 90-100% relative humidity.

(b) Residual curative action

After a cultivation period of three weeks, tomato plants were infested with a suspension of sporangia of the fungus. After an incubation of 22 hours in a moist chamber at 20° with 90-100% relative humidity, the infested plants were dried, and subsequently sprayed with a spray liquor prepared, as described in the foregoing, from wettable powder of the active substance (0.02% of active substance, for example one of the compounds from Tables 1 to 5). After drying of the applied coating, the treated plants were returned to the moist chamber. An assessment of fungus infection was made 5 days after infestation.

(c) Systemic action

A spray liquor prepared, as described in the foregoing, from wettable powder of the active substance [0.002% of active substance (for example one of the compounds from Tables 1 to 5), relative to the volume of soil], was applied to the soil in which tomato plants had been cultivated for 3 weeks. Care was taken to ensure that the spray liquor did not come into contact with the parts of the plants above the soil. After 48 hours, the treated plants were infested with a suspension of sporangia of the fungus. An assessment of fungus infection was made after incubation of the infested plants for 5 days at 20° with 90-100% relative humidity.

The compounds of the formula I exhibited in the above tests against Phytophthora pathogens not only an excellent residual-protective action and residual-curative action, but also a very good systemic action. They reduced infection to less than 20%. Infection was prevented completely on application of the following compounds Nos. 1.1, 1.15, 1.17, 1.24 to 1.34, 2.1 to 2.5, 2.10, 2.13, 2.19, 2.32 to 2.48, 3.1, 3.4, 3.9, 3.10, 3.25 to 3.31, 4.2, 4.4, 4.9, 4.14, 5.1 and 5.2.

EXAMPLE 9

Action against Pythium debaryanum on sugar beet (a) Action after soil application The fungus was cultivated on a carrot-chips nutrient solution, and applied to a soil/sand mixture. The soil infested in this manner was placed into flower pots, and sown with sugar-beet seeds. Immediately after sowing, the test preparations, formulated as wettable powders, were poured as aqueous suspensions over the soil (20 ppm of one of the compounds from Tables 1 to 5, relative to the volume of soil). The pots were subsequently left for 2-3 weeks in a greenhouse at about 20°. The soil was continuously maintained moist by light spraying. In the evaluation of the test results, the sprouting of the sugar-beet plants and also the proportion of healthy plants and diseased plants were determined.

(b) Action after dressing application

The fungus was cultivated on a carrot-chips nutrient solution and then applied to a soil/sand mixture. The soil infested in this manner was placed into soil trays, and sown with sugar-beet seeds which had been dressed with the test preparations formulated as dressing powder (0.06% of one of the compounds from Tables 1 to 5). The sown trays were left for 2-3 weeks in a greenhouse at about 20°. The soil was maintained uniformly moist by light spraying. In the evaluation of the results, the sprouting of the sugar-beet plants was determined. After treatment with compounds of the formula I, especially with those of the subgroups Ic and Id, over 85% of the sugar-beet seeds emerged and the plants had a healthy appearance.

The compounds Nos. 1.25, 2.1 to 2.13, 2.19, 2.32 to 2.48, 3.4, 3.10, 4.2, 4.3, 4.4, 4.9, 4.14, 5.1, 5.2 and 5.6 exhibited in the above tests a very good action against Pythium pathogens on sugar-beet plants (emergence of plants 92-95%, as in the case of control plants which had not been infested).

An equally good action was achieved against Pythium pathogens on maize plants in analogous tests.

What is claimed is:

1. A homoserine derivative of the formula I

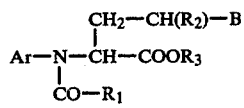

wherein $R_1$ is alkyl of 2 to 6 carbon atoms which is optionally interrupted by an oxygen or a sulfur atom, 2-furyl, 2-tetrahydrofuryl, 1H-1,2,4-triazolylmethyl, 1-imidazolylmethyl, 1-pyrazolylmethyl, $C_2$-$C_4$-alkenyl or cyclopropyl, each of which is unsubstituted or is substituted by halogen, or when B is halogen, $R_1$ may also be halomethyl, $R_2$ is hydrogen or methyl; $R_3$ is hydrogen or $C_1$-$C_4$-alkyl; Ar is

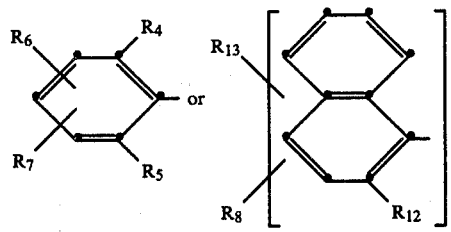

in which $R_4$ is $C_1$-$C_3$-alkyl, $C_1$-$C_3$-alkoxy or halogen, $R_5$ is $C_1$-$C_3$-alkyl, $C_1$-$C_3$-alkoxy, $NH_2$, halogen or $NO_2$, $R_6$ is hydrogen, $NO_2$, $NH_2$, $C_1$-$C_3$-alkyl, $C_1$-$C_3$-alkoxy or halogen, $R_7$ and $R_8$ are each hydrogen or methyl, $R_{12}$ is methyl, $NO_2$ or $NH_2$, $R_{13}$ is hydrogen, methyl, $NO_2$ or $NH_2$; and B is one of the following groups $-X(O)_kH$, $-X(O)_mR_9$,

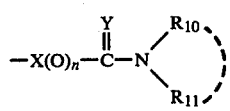

or halogen, wherein X and Y independently of one another are each oxygen or sulfur, and, when X is sulfur, k has the value nought or 3, and n and m are nought, 1 or 2, whilst when X is oxygen k, m and n are always nought, $R_9$ is a $C_1$-$C_5$-alkyl group which is unsubstituted or substituted by halogen, $C_1$-$C_3$-alkoxy or $C_1$-$C_3$-alkylthio, $R_{10}$ is hydrogen, methyl or ethyl, $R_{11}$ is a $C_1$-$C_5$-alkyl group which is unsubstituted or substituted by halogen, or $R_{11}$ is a phenyl group which is unsubstituted or substituted by halogen, methyl, trifluoromethyl or nitro, or $R_{10}$ and $R_{11}$ together with the nitrogen atom to which they are bound form an imidazole or 1,2,4-triazole ring.

2. A homoserine derivative according to claim 1, wherein Ar is

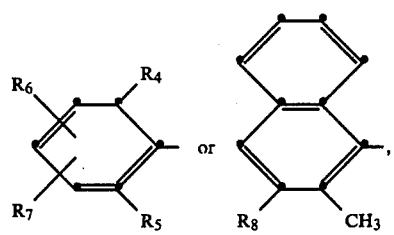

wherein $R_5$ is $C_1$-$C_3$-alkyl, $C_1$-$C_3$-alkoxy or halogen, $R_6$ is hydrogen, $C_1$-$C_3$-alkyl, $C_1$-$C_3$-alkoxy or halogen, and $R_7$ and $R_8$ are each hydrogen or methyl.

3. A homoserine derivative according to claim 1, wherein $R_1$ is $C_1$-$C_3$-alkoxymethyl, 2-furyl or 2-tetrahydrofuryl; $R_2$ and $R_3$ are hydrogen; B is OH, SH or $SO_3H$; and Ar is substituted phenyl in which $R_4$ is $C_1$-$C_3$-alkyl, $C_1$-$C_3$-alkoxy or halogen, $R_5$ is $C_1$-$C_3$-alkyl, $C_1$-$C_3$-alkoxy, halogen or nitro, $R_6$ is hydrogen or $C_1$-$C_3$-alkyl, and $R_7$ is hydrogen or methyl.

4. A homoserine derivative according to claim 1, wherein $R_1$ is $C_1$-$C_3$-alkoxymethyl, 2-furyl or 2-tetrahydrofuryl; $R_2$ is hydrogen; $R_3$ is $C_1$-$C_3$-alkyl; B is $OR_9$, in which $R_9$ is a $C_1$-$C_3$-alkyl group which is unsubstituted or substituted by halogen; and Ar is substituted phenyl in which $R_4$ is $C_1$-$C_3$-alkyl, $C_1$-$C_3$-alkoxy or halogen, $R_5$ is $C_1$-$C_3$-alkyl, $C_1$-$C_3$-alkoxy or halogen, $R_6$ is hydrogen or $C_1$-$C_3$-alkyl, and $R_7$ is hydrogen or methyl.

5. A homoserine derivative according to claim 1, wherein $R_1$ is $C_1$-$C_2$-alkoxymethyl or 2-tetrahydrofuryl; $R_2$ is hydrogen; $R_3$ is hydrogen or methyl; B is OH or methoxy; and Ar is substituted phenyl in which $R_4$ is methyl, $R_5$ is methyl, chlorine, $NO_2$ or $NH_2$, $R_6$ is hydrogen, methyl, chlorine, $NO_2$ or $NH_2$, and $R_7$ is hydrogen or methyl.

6. A homoserine derivative according to claim 1, $R_1$ is $C_1$-$C_2$-alkoxymethyl or 2-tetrahydrofuryl; $R_2$ is hydrogen; $R_3$ is hydrogen or methyl; B is OH or methoxy; where Ar is substituted α-naphthyl in which is hydrogen or 3-methyl, $R_{12}$ is methyl, $NO_2$ or $NH_2$, and $R_{13}$ is hydrogen, methyl, $NO_2$ or $NH_2$.

7. A homoserine derivative according to claim 6, wherein $R_{13}$ is hydrogen, 4—$NO_2$ or 4—$NH_2$.

8. A homoserine derivative according to claim 5, wherein $R_1$ is 2-tetrahydrofuryl.

9. A homoserine derivative according to claim 6, wherein $R_1$ is 2-tetrahydrofuryl.

10. N-(2,6-Dimethylphenyl)-N-methoxyacetyl-homoserine-methyl ester according to claim 5.

11. N-(2,6-Dimethylphenyl)-N-methoxyacetyl-homoserine-ethyl ester according to claim 5.

12. N-(2,3,6-Trimethylphenyl)-N-methoxyacetyl-homoserine-methyl ester according to claim 5.

13. N-(2,6-Dimethylphenyl)-N-methoxyacetyl-[4-(imidazol-1-yl)-carbonyloxy]-butyric acid methyl ester according to claim 2.

14. N-(2-Methylnaphthyl)-N-methoxyacetyl-homoserinemethyl ester according to claim 2.

15. N-(2-Methylnaphthyl)-N-(tetrahydrofurylcarbonyl)-homoserine-methyl ester according to claim 9.

16. N-(2,6-Dimethyl-3-chlorophenyl)-N-methoxyacetyl-homoserine methyl ester according to claim 5.

17. N-(2,3,6-Trimethylphenyl)-N-methoxyacetyl-homoserine ethyl ester according to claim 2.

18. N-(2,3,6-Trimethylphenyl)-N-methoxyacetyl-4-methoxy-2-aminobutyric acid methyl ester according to claim 5.

19. N-(2,3,6-Trimethylphenyl)-N-methoxyacetyl-4-(N'-methylcarbamoyloxy)-1-aminobutyric acid methyl ester according to claim 2.

20. N-(2-Methylnaphthyl)-N-methoxyacetyl-4-(N'-methylcarbamoyloxy)-2-aminobutyric acid methyl ester according to claim 2.

21. N-(2,6-dimethylphenyl)-N-methoxyacetyl-2-amino-4-chlorobutyric acid methyl ester according to claim 2.

22. N-(2,6-dimethyl-3-chlorophenyl)-N-methoxyacetyl-2-amino-4-chlorobutyric acid ethyl ester according to claim 2.

23. N-(2,6-dimethylphenyl)-N-methoxyacetyl-2-amino-4-bromobutyric acid ethyl ester according to claim 2.

24. N-(2-methylnaphthyl)-N-methoxyacetyl-2-amino-4-chlorobutyric acid ethyl ester according to claim 2.

25. A composition for combating and/or preventing an infection by pathogenic microorganisms, which comprises as active ingredient an effective amount of a compound according to claim 1, together with a suitable carrier therefor.

26. A method of combating and/or preventing infection caused by pathogenic microorganisms, which method comprises applying to the locus to be protected an effective amount of a compound according to claim 1.

27. A method of combatting and/or preventing infection caused by pathogenic microorganisms, which method comprises applying to the locus to be protected an effective amount of a compound according to claim 2.

28. A method of combatting and/or preventing infection caused by pathogenic microorganisms, which method comprises applying to the locus to be protected an effective amount of the compound according to claim 13.

29. A method of combatting and/or preventing infection caused by pathogenic microorganisms, which method comprises applying to the locus to be protected an effective amount of the compound according to claim 17.

30. A method of combatting and/or preventing infection caused by pathogenic microorganisms, which method comprises applying to the locus to be protected an effective amount of the compound according to claim 19.

31. A method of combatting and/or preventing infection caused by pathogenic microorganisms, which method comprises applying to the locus to be protected an effective amount of the compound according to claim 20.

32. A method of combatting and/or preventing infection caused by pathogenic microorganisms, which method comprises applying to the locus to be protected an effective amount of a compound according to claim 3.

33. A method of combatting and/or preventing infection caused by pathogenic microorganisms, which method comprises applying to the locus to be protected an effective amount of a compound according to claim 4.

34. A method of combatting and/or preventing infection caused by pathogenic microorganisms, which method comprises applying to the locus to be protected an effective amount of a compound according to claim 5.

35. A method of combatting and/or preventing infection caused by pathogenic microorganisms, which method comprises applying to the locus to be protected an effective amount of the compound according to claim 10.

36. A method of combatting and/or preventing infection caused by pathogenic microorganisms, which method comprises applying to the locus to be protected an effective amount of the compound according to claim 11.

37. A method of combatting and/or preventing infection caused by pathogenic microorganisms, which method comprises applying to the locus to be protected an effective amount of the compound according to claim 12.

38. A method of combatting and/or preventing infection caused by pathogenic microorganisms, which method comprises applying to the locus to be protected an effective amount of the compound according to claim 16.

39. A method of combatting and/or preventing infection caused by pathogenic microorganisms, which method comprises applying to the locus to be protected an effective amount of the compound according to claim 18.

40. A method of combatting and/or preventing infection caused by pathogenic microorganisms, which method comprises applying to the locus to be protected an effective amount of a compound according to claim 8.

41. A method of combatting and/or preventing infection caused by pathogenic microorganisms, which method comprises applying to the locus to be protected an effective amount of a compound according to claim 6.

42. A method of combatting and/or preventing infection caused by pathogenic microorganisms, which method comprises applying to the locus to be protected an effective amount of the compound according to claim 14.

43. A method of combatting and/or preventing infection caused by pathogenic microorganisms, which method comprises applying to the locus to be protected an effective amount of a compound according to claim 7.

44. A method of combatting and/or preventing infection caused by pathogenic microorganisms, which method comprises applying to the locus to be protected an effective amount of a compound according to claim 9.

45. A method of combatting and/or preventing infection caused by pathogenic microorganisms, which method comprises applying to the locus to be protected an effective amount of the compound according to claim 15.

46. A method of combatting and/or preventing infection caused by pathogenic microorganisms, which method comprises applying to the locus to be protected an effective amount of the compound according to claim 21.

47. A method of combatting and/or preventing infection caused by phathogenic microorganisms, which method comprises applying to the locus to be protected an effective amount of the compound according to claim 22.

48. A method of combatting and/or preventing infection caused by pathogenic microorganisms, which method comprises applying to the locus to be protected an effective amount of the compound according to claim 23.

49. A method of combatting and/or preventing infection caused by pathogenic microorganisms, which method comprises applying to the locus to be protected an effective amount of the compound according to claim 24.

* * * * *